US011735324B2

(12) United States Patent
Mishra et al.

(10) Patent No.: US 11,735,324 B2
(45) Date of Patent: Aug. 22, 2023

(54) TWO-WAY QUESTIONNAIRE GENERATION FOR MEDICAL COMMUNICATION

(71) Applicant: INTERNATIONAL BUSINESS MACHINES CORPORATION, Armonk, NY (US)

(72) Inventors: Sunil K. Mishra, Morrisville, NC (US); Arvin Bhatnagar, Cary, NC (US)

(73) Assignee: International Business Machines Corporation, Armonk, NY (US)

( * ) Notice: Subject to any disclaimer, the term of this patent is extended or adjusted under 35 U.S.C. 154(b) by 281 days.

(21) Appl. No.: 17/029,106

(22) Filed: Sep. 23, 2020

(65) Prior Publication Data
US 2022/0093278 A1 Mar. 24, 2022

(51) Int. Cl.
*G16H 80/00* (2018.01)
*G16H 10/60* (2018.01)
*G16H 10/20* (2018.01)
*G06F 40/103* (2020.01)
*G06Q 10/10* (2023.01)
*G06N 20/00* (2019.01)
*G16H 50/70* (2018.01)

(52) U.S. Cl.
CPC ........... *G16H 80/00* (2018.01); *G06F 40/103* (2020.01); *G06N 20/00* (2019.01); *G06Q 10/10* (2013.01); *G16H 10/20* (2018.01); *G16H 10/60* (2018.01); *G16H 50/70* (2018.01)

(58) Field of Classification Search
CPC ......... G16H 10/60; G16H 50/70; G16H 10/20
USPC ........................................................... 705/3
See application file for complete search history.

(56) References Cited

U.S. PATENT DOCUMENTS

| 11,468,993 | B2 * | 10/2022 | Koplin | G06N 5/022 |
| 2002/0010596 | A1 * | 1/2002 | Matory | A61B 5/0002 705/2 |
| 2002/0022975 | A1 * | 2/2002 | Blasingame | G16H 10/20 705/3 |
| 2002/0035486 | A1 | 3/2002 | Huyn | |

(Continued)

FOREIGN PATENT DOCUMENTS

| WO | 2014039881 A1 | 3/2014 |
| WO | 2019140275 A1 | 7/2019 |

OTHER PUBLICATIONS

Lobach et al., "Adapting the Human-Computer Interface for Reading Literacy and Computer Skill to Facilitate Collection of Information Directly from Patients." Series: Studies in Health Technology and Informatics Ebook, vol. 107: MEDINFO 2004, pp. 1142-1146, http://ebooks.iospress.nl/volumearticle/21171.

(Continued)

*Primary Examiner* — Peter H Choi
*Assistant Examiner* — Rachael Sojin Stone
(74) *Attorney, Agent, or Firm* — Caleb D. Wilkes

(57) ABSTRACT

A method, a computer system, and a computer program product for two-way document generation for medical communication are provided. Patient data from a patient may be received. Medical services provider data from a medical services provider may be received. The patient data and the medical services provider data may be run through a machine learning model so that the machine learning model may produce a first document and a second document. The first document may be presented to the patient. The second document may be presented to the medical services provider.

19 Claims, 5 Drawing Sheets

(56) References Cited

U.S. PATENT DOCUMENTS

| | | | |
|---|---|---|---|
| 2002/0143578 A1* | 10/2002 | Cole | G16H 70/60 705/2 |
| 2002/0156654 A1* | 10/2002 | Roe | G16H 40/67 705/3 |
| 2002/0184050 A1 | 12/2002 | Papageorge | |
| 2003/0004788 A1 | 1/2003 | Edmundson | |
| 2005/0149359 A1* | 7/2005 | Steinberg | G16H 50/20 705/2 |
| 2007/0038480 A1* | 2/2007 | Kay | G16H 10/60 706/45 |
| 2009/0037223 A1* | 2/2009 | Green | G16H 10/60 705/2 |
| 2011/0137675 A1 | 6/2011 | McLaughlin | |
| 2011/0224493 A1 | 9/2011 | Oyadiran | |
| 2014/0229199 A1 | 8/2014 | Beckley | |
| 2015/0046183 A1* | 2/2015 | Cireddu | G16H 10/60 705/3 |
| 2016/0342771 A1 | 11/2016 | Deng | |
| 2018/0046772 A1* | 2/2018 | Mitteldorf | A61B 5/0022 |
| 2018/0181713 A1* | 6/2018 | Pillarisetty | G16H 10/60 |
| 2018/0366221 A1* | 12/2018 | Crehore | G06F 16/211 |
| 2022/0323766 A1* | 10/2022 | Hughes | A61N 1/0551 |

OTHER PUBLICATIONS

McCarthy, "7 smartphone apps that can help improve health literacy," NueMD, Industry News, Healthcare Technology, https://www.nuemd.com/news/2017/08/03/7-smartphone-apps-can-help-improve-health-literacy, accessed Jul. 14, 2020, 8 pages.

Kortum et al., "A Dynamic Adaptive Questionnaire for Improved Disease Diagnostics." Springer International Publishing AG 2017, N. Adams et al. (Eds.) IDA 2017. LNCS, vol. 10584, pp. 162-172, 2017.

Mell et al., "The NIST Definition of Cloud Computing", National Institute of Standards and Technology, Special Publication 800-145, Sep. 2011, 7 pages.

* cited by examiner

TWO-WAY QUESTIONNAIRE GENERATION FOR MEDICAL COMMUNICATION

BACKGROUND

The present invention relates generally to the field of artificial intelligence for health care, and more particularly to artificial intelligence for improving doctor-patient communications.

SUMMARY

According to one exemplary embodiment, a method, a computer system, and a computer program product are provided for two-way document generation for medical communication. Patient data from a patient may be received. Medical services provider data from a medical services provider may be received. The patient data and the medical services provider data may be run through a machine learning model so that the machine learning model may produce a first document and a second document. The first document may be presented to the patient. The second document may be presented to the medical services provider.

BRIEF DESCRIPTION OF THE DRAWINGS

These and other objects, features and advantages of the present invention will become apparent from the following detailed description of illustrative embodiments thereof, which is to be read in connection with the accompanying drawings. The various features of the drawings are not to scale as the illustrations are for clarity in facilitating one skilled in the art in understanding the invention in conjunction with the detailed description. In the drawings.

DETAILED DESCRIPTION

Detailed embodiments of the claimed structures and methods are disclosed herein; however, it can be understood that the disclosed embodiments are merely illustrative of the claimed structures and methods that may be embodied in various forms. This invention may, however, be embodied in many different forms and should not be construed as limited to the exemplary embodiments set forth herein. Rather, these exemplary embodiments are provided so that this disclosure will be thorough and complete and will fully convey the scope of this invention to those skilled in the art. In the description, details of well-known features and techniques may be omitted to avoid unnecessarily obscuring the presented embodiments.

The following described exemplary embodiments provide a system, a method and a computer program product for two-way document generation for medical communication. As such, the present embodiment has the capacity to improve the technical field of medical artificial intelligence by helping improve communication between patients and medical services providers such as doctors.

Effective communication between a patient and a medical services provider is essential for positive healthcare outcomes. Patients and medical services providers struggle with the correct set of questions to ask each other that would maximize the benefits of their limited interaction time or check-up time. Doctors are often busy checking on many patients and running a practice, and often have fifteen minutes of less to spend with each patient.

Health literacy is the ability to obtain, understand, and follow the necessary health information. As per health.gov, only 12% of Americans have proficiency in healthcare literacy. People from certain socioeconomic groups or geographic regions or neighborhoods can have particular struggles or challenges with health literacy.

Thus, there is a need to use artificial intelligence to help improve the communication between patients and medical services providers, to help patients improve their health literacy, to help medical services providers more quickly find origins of health problems, and to help medical services providers and patients more quickly identify appropriate health treatments.

The proposed method and system will acquire data from various data sets, such as personal health records of a patient, information related to the social determinant of an individual or patient, and information related to demographic data of the individual or patient. Artificial intelligence ("AI") and machine learning ("ML") algorithms may combine all the data features and come up with two sets of questionnaires—one for the medical services provider and one for the patient. The collection of questionnaires may help medical service providers to probe with effective and relevant questions and may help educate patients about their health conditions.

Figure 1:
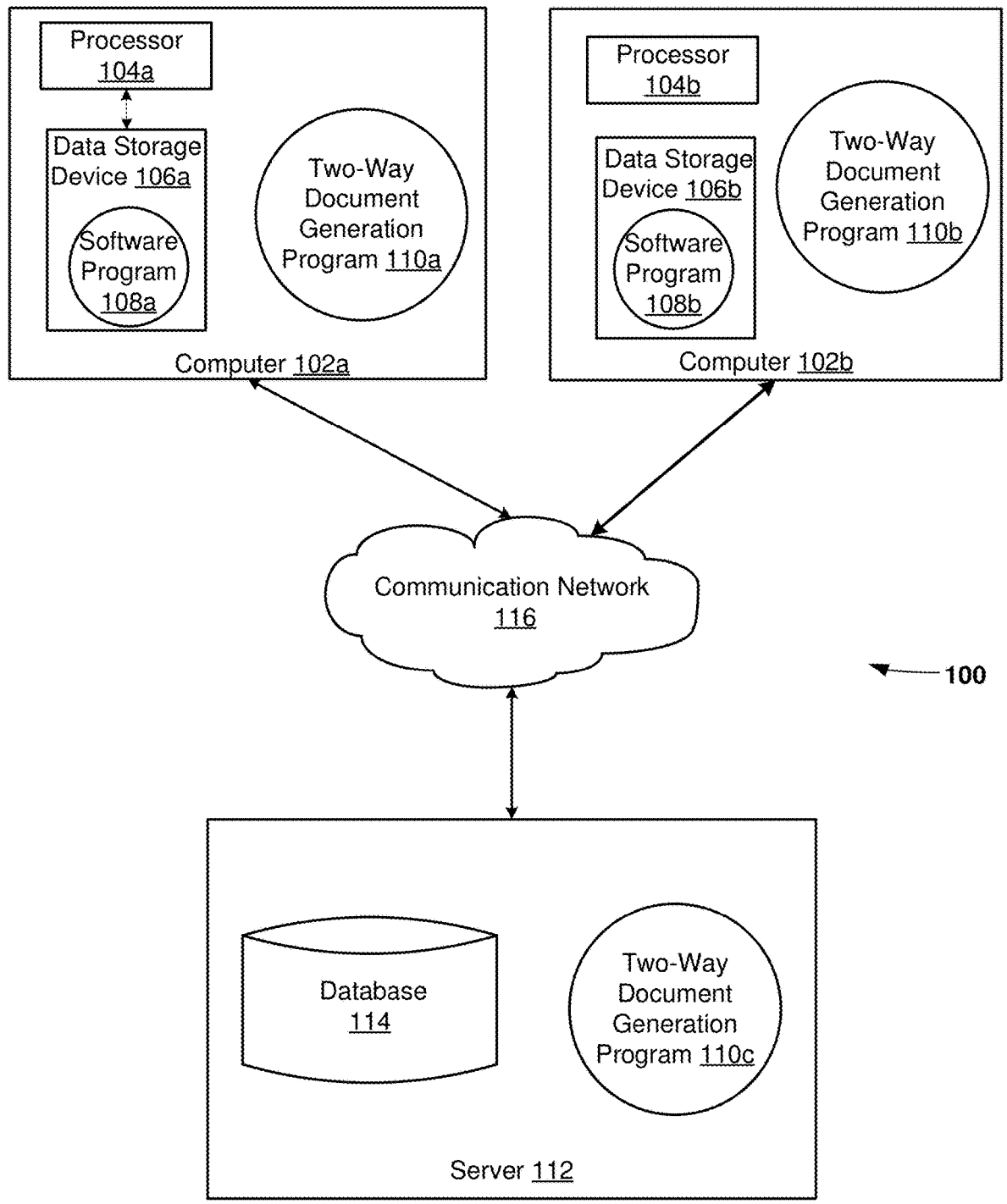
FIG. 1 illustrates a networked computer environment according to at least one embodiment.

Referring to FIG. 1, an exemplary networked computer environment 100 in accordance with one embodiment is depicted. The networked computer environment 100 may include a first computer 102a with a first processor 104a and a first data storage device 106a that is enabled to run a first software program 108a and a two-way document generation program 110a. The networked computer environment 100 may include a second computer 102b with a second processor 104b and a second data storage device 106b that is enabled to run a second software program 108b and a two-way document generation program 110b. The networked computer environment 100 may also include a server 112 that is enabled to run a two-way document generation program 110c that may interact with a database 114 and a communication network 116. The networked computer environment 100 may include one or more computers in addition to the first and second computers 102a, 102b and may include a plurality of servers 112, only one of which is shown. The communication network 116 may include various types of communication networks, such as a wide area network (WAN), local area network (LAN), a telecommunication network, a wireless network, a public switched network and/or a satellite network. It should be appreciated that FIG. 1 provides only an illustration of one implementation and does not imply any limitations with regard to the environments in which different embodiments may be implemented. Many modifications to the depicted environments may be made based on design and implementation requirements.

The first and second computers 102a, 102b may be client computers and may communicate with the server computer 112 via the communications network 116. The communications network 116 may include connections, such as wire, wireless communication links, or fiber optic cables. As will be discussed with reference to FIG. 4, the server 112 may include internal components 902a and external components 904a, respectively, and the first and the second computers 102a, 102b may include, respectively, internal components 902b and external components 904b. The server 112 may also operate in a cloud computing service model, such as Software as a Service (SaaS), Platform as a Service (PaaS), or Infrastructure as a Service (IaaS). The server 112 may also be located in a cloud computing deployment model, such as a private cloud, community cloud, public cloud, or hybrid cloud. The first and the second computers 102a, 102b may, respectively, be, for example, a mobile device, a telephone, a personal digital assistant, a netbook, a laptop computer, a tablet computer, a desktop computer, or any type of computing device capable of running a program, accessing a network, and accessing a database 114. According to various implementations of the present embodiment, the two-way document generation program 110a, 110b, 110c may interact with a database 114 that may be embedded in various storage devices, such as, but not limited to the first and/or the second computers 102a, 102b, a server 112 connected to a network, or a cloud storage service.

According to the present embodiment, a user using a first computer 102a, a second computer 102b, or a server computer 112 may use the two-way document generation program 110a, 110b, 110c to perform two-way document generation for medical communication. The two-way document generation method is explained in more detail below with respect to FIG. 2.

Figure 2:
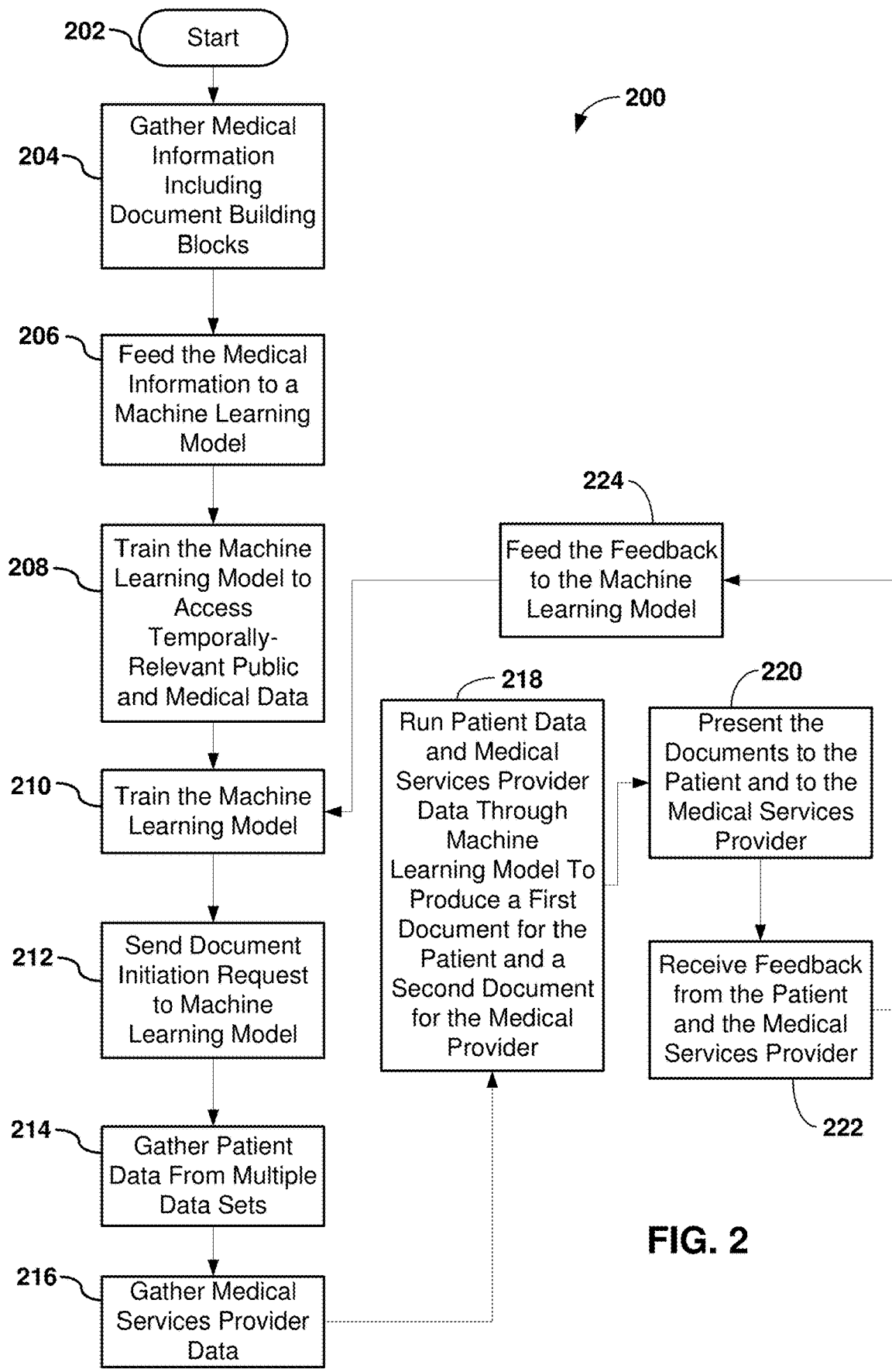
FIG. 2 is an operational flowchart illustrating a process for two-way document generation for medical communication according to at least one embodiment.

Referring now to FIG. 2, an operational flowchart illustrating the exemplary two-way document generation process 200 used by the two-way document generation program 110a, 110b, 110d according to at least one embodiment is depicted.

It may be appreciated that FIG. 2 provides only an illustration of one embodiment and does not imply any limitations with regard to how different embodiments may be implemented. Many modifications to the depicted embodiment(s) may be made based on design and implementation requirements.

As described in embodiments above, the two-way document generation program 110a, 110b, 110c may improve the functionality of health care artificial intelligence by using machine learning to help prepare medical service providers and doctors as well as patients for medical exams and checkups. This preparation of the patients may help them improve their health literacy.

In step 202 of process 200 shown in FIG. 2, the process 200 is started.

In step 204 of process 200 shown in FIG. 2, medical information is gathered. The medical information includes building blocks for generating documents. Web crawling or web scraping may be used to perform the gathering of step 204. If a medical practice seeks to perform the method to develop its own two-way document generator, then the medical practice can upload all of its existing physical or electronic medical documents into a memory, e.g., into memory in database 114 or into the data storage devices 106a, 106b. Web crawling or web scraping may also be used to gather medical documents that can be stored as part of step 204 and saved for usage in further steps of the process 200.

The medical information that is gathered may include data that links symptoms with diagnoses and with possible treatments to remedy the symptoms and the causes of the symptoms. The medical information may also include anatomical information including information about anatomies of healthy individuals as compared to anatomies of patients with certain disease or problematic health conditions. The medical information may also include information about proper medical terminology as well as local colloquial terminology for the body and certain health conditions. Medical studies, medical literature, and medical textbooks may be sources of information for the gathering of the medical information in step 204. The above-mentioned medical information may constitute building blocks for generating documents and questionnaires. Building blocks for generating documents and questionnaires may also include general health questions or specific questions related to a particular medical specialty and may relate to general health practices of a patient or to specific symptoms of a patient.

All or some of the medical information may be stored in database 114 or in the data storage devices 106a, 106b.

In step 206 of process 200 shown in FIG. 2, the medical information is fed to a machine learning model. In at least some embodiments of the disclosure, the machine learning model is a deep learning model. Machine learning models use algorithms to search and interpret data, to learn from that data, and to make enlightened decisions according to the learning. Deep learning models are types of machine learning models and use algorithms in layers to create an artificial neural network that can learn and make intelligent decisions on its own. Both machine learning and deep learning are types of artificial intelligence, but deep learning may in many instances be more human-like than machine learning.

In step 206, the medical information may be fed to various types of deep learning networks such as an unsupervised pre-trained model, a convolutional neural network, a recurrent neural network, or a recursive neural network. The feeding of the medical information may include pre-processing of the information. Obtaining a machine learning model may include importing one or more deep learning programming-language libraries. The machine learning model may perform natural language processing (NLP) techniques to parse out data from the medical information in an appropriate data form to feed to the machine learning model. The machine learning model may include algorithms such as linear regression algorithms, logical regression algorithms, classification and regression trees, K-nearest neighbor algorithms, and naïve bayes algorithms.

In step 208 of process 200 shown in FIG. 2, the machine learning model is trained to access temporally-relevant public and medical data. The temporally-relevant public and medical data may be referred to as temporal data. Some public information such as weather changes, pollen changes, and air quality levels change frequently and can provide insight to medical services providers or doctors as to what symptoms or medical conditions in patients might be caused or exacerbated by such weather changes, pollen changes, air quality levels, etc. During a pandemic, trends in positive cases may be updated and publicized frequently and may provide clues to medical personnel about causes, origins, non-causes, or non-origins of certain symptoms. Public databases, such as websites accessible to the general public, may provide regular updates on such changing public information. Therefore, some embodiments include the training of the machine learning model to regularly search for such public information. By training the machine learning model to regularly check for and incorporate updates from public data and medical data, the machine learning model may reduce the data load that it must save and may also capitalize on computing and calculating resources that are performed by other outside entities such as government entities who provide relevant public health information.

This accessing of step 208 may also include receiving updates of new medical diagnoses, possible treatments, and new symptoms that may rapidly emerge, e.g., during a public health pandemic. Certain web addresses and desired data types are provided to the machine learning model to enable the model to regularly search and glean information from the internet to add to the machine learning model for use in subsequent steps of process 200, e.g., for use in two-way generating of documents. The machine learning model may be trained to search, e.g., search the internet, for updates to public medical information on a frequent, scheduled basis, e.g., on a daily basis, a weekly basis, or on a twice-daily basis, etc.

In step 210 of process 200 shown in FIG. 2, the machine learning model is trained. Training a machine learning model includes providing a desired output set and allowing the model to find patterns in the desired output set that can be used to map input data that will result in the desired output set. For example, for the training a desired set of documents—a first one for a patient and a second one for a medical services provider, e.g., a doctor—may be fed to the model and the model parses through the desired set to find patterns that are relevant to certain input data. Training may also include a medical services provider verifying for the system that input data that includes certain symptoms triggers generation of a document with questions related to those symptoms. Training may also include the medical services provider verifying for the system that input data indicating that the patient belongs to a certain socioeconomic group or lives or works in a certain geographical region or neighborhood triggers the generation of a document which uses basic medical terminology. The training may also include the medical services provider verifying that sets of documents generated for the medical services provider have levels of detail appropriate for the identity of the medical services provider, e.g., whether the medical services provider receiving the document is a doctor, a physician assistant, a nurse, a nurse assistant, or an administrator, etc.

In step 212 of process 200 shown in FIG. 2, a two-way document-initiation or document-generation request is sent to the deep learning model. The two-way document-initiation request may be sent from (1) a first party, e.g., from a patient, who is using the first computer 102a that hosts two-way document generation program 110a to (2) a computer, e.g., server 112, that hosts the two-way document generation program 110c. A patient may download two-way document generation program 110a to a smart phone of the patient, and then may trigger the document-initiation request of step 212 by accessing the two-way document generation program 110a. The document-initiation request may be programmed as being mandatory in order to contact a medical facility to schedule appointment. In other words, the medical services provider may add the two-way document generation program 110b to its main website so that the request of step 212 is triggered when a patient contacts the medical services provider to schedule an appointment. The server 112 hosting the two-way document-generation program 110c may be hosted at an office of the medical services provider or may be hosted remotely in the cloud.

In some embodiments, the second computer 102b is located at the medical facility of the medical services provider, and a medical services provider triggers the request of step 212 after the patient comes to the facility or shortly in advance of an appointment when the patient is scheduled to arrive at the medical facility. The two-way document-initiation request may be sent from (1) a second party, e.g., from a medical services provider, who is using the second computer 102b that hosts two-way document generation program 110b to (2) a computer, e.g., server 112, that hosts the two-way document generation program 110c. A medical services provider may download two-way document generation program 110b to a smart phone or office computing device of the medical services provider.

In at least some embodiments, the request of step 212 includes information indicating the identity of the patient and of the medical services provider from whom the patient is seeking medical assistance or medical advisement. The identity information may include a name, gender, residence, age, work location, profession, native language, language proficiency, etc. of the patient. When the two-way document generation program 110a has been installed on a first computer 102a, e.g., on a smart phone, of the patient, the triggering of the request may prompt the two-way document generation program 110a to send a prompt through the first computer 102a to request to retrieve data from the first computer 102a itself that will help identify the patient and help the medical services provider more quickly make a diagnosis and medical intervention recommendation. For example, the two-way document generation program 110a on a smart phone may request via the smart phone that the user of the smart phone allow the two-way document generation program 110a to have access to a social media profile of the user that is stored on or accessible via the smart phone, with the user being the prospective medical patient. This data may help the two-way document generation program 110b glean information about the health literacy of a patient, about possible health conditions that the patient may have in common with others from their own socioeconomic group or ethnic background, and perhaps even of symptoms of the patient.

The request may be sent via the communication network 116 from one computer to another computer, e.g., from the first computer 102a to the server 112 or from the second computer 102b to the server 112.

In step 214 of process 200 shown in FIG. 2, patient data is gathered from multiple sets.

In at least some embodiments, patient data may be gathered that is provided along with the request of step 212. In some embodiments, that patient data that is provided along with the request of step 212 includes information about current symptoms or the health status of the patient or prospective patient. In some embodiments, the request of step 212 from a patient includes GPS or GNSS data from the computing device, e.g., the first computer 102a, of the patient which may provide data about the geographical location of residence or employment of the patient. In some embodiments, the first computer 102a is a fitness device kept or worn by the patient and tracks health features of the patient such as heart rate and number of steps taken in a day. This information from the fitness device may be transmitted from the first computer 102a to the server 112 as patient data.

In at least some embodiments, the medical services provider may already be familiar with a patient and may have treated that patient in the past or provided medical advice to that patient in the past. Therefore, the two-way document generation program 110b may request access to retrieve patient data from medical records stored in a database of the medical services provider, e.g., in a data storage device 106b of a second computer 102b located at a medical office.

In addition, as a part of step 214 the two-way document generation program 110a, 110c may use patient identity information provided with the request of step 212 to search public record databases to find additional patient data regarding the patient. For example, the two-way document generation program 110a, 110c may use the patient identity information to look up information about a place of residence of the patient, place of work of the patient, income of the patient, education levels of the patient, etc. In some instances, a patient will be involved in the request of step 212 who has previously accessed the two-way document generation program 110c, and so the gathering of step 214 may include the two-way document generation program 110c accessing its own data storage, e.g., in database 114, to acquire patient data to help with the subsequent steps of the process 200. Patient data may also include information about familial relations of a patient, e.g., whether a patient is a parent, recently had a child, chronic health conditions running in the family, etc.

In step 216 of process 200 shown in FIG. 2, medical services provider data is gathered. In at least some embodiments, the medical services provider seeking to use the two-way document generation program 110c will have already registered with the two-way document generation program 110c and have provided data regarding the medical services provider, their employees, their specialty or specialties, health tendencies of their patients, etc. For example, stored in the database 114 of the two-way document generation program 110c may be information about whether doctors, physician assistants, nurses, nurse assistants, and administrators work at the medical services provider office, how many work at the medical services provider office, and optionally the names of the medical services providers including their employees.

In embodiments where the medical services provider triggers the request of step 212 to the two-way document generation program 110c, the request may also send information about the particular medical worker or workers who will be seeing or communicating with the patient. The two-way document generation program 110c may then as part of step 216 trace the identity of the medical worker in the medical worker data stored in their system to facilitate expeditious gathering of data regarding the particular medical care worker for whom one of the documents will be provided. Because a medical services provider will in some embodiments use the two-way document generation program 110b, 110c more often than the patient will use the two-way document generation program 110a, 110c, the two-way document generation program 110c may have more opportunities to gather and store information about the medical services provider than about the patient.

The medical services provider data that is gathered in step 216 may include information about knowledge of the particular worker or provider with respect to certain health conditions and common or uncommon health conditions or illness symptoms. In some instances when the two-way document generation program 110c has not previously interacted with a medical services provider who then seeks to use the two-way document generation program 110b, 110c for a first time, the two-way document generation program 110c may use medical services provider identity information provided with the request of step 212 to search public record databases to find additional medical services provider data regarding the specialties or health focuses of the medical services provider. This medical services provider data may, for example, include a physical location of the medical services provider office or a location of a bulk of patients that frequent the medical services provider office or a type of practice of the medical services provider, e.g., whether the medical care provider is a pediatrician, a physical therapist, an obstetrician-gynecologist, or an ear-nose-throat specialist, etc.

In step 218 of process 200 shown in FIG. 2, the patient data and the medical services provider data are run through or fed into the deep learning model such that the machine learning model produces a first document for the patient and a second document for the medical services provider. In at least some embodiments, the first document will be different than the second document. The first document may be tailored to be read or listened to by the patient and the second document may be tailored to be read or listened to by the medical services provider. As part of step 218, based on the training received in step 210 the two-way document generation program 110b may web crawl or web scrape and may access and retrieve temporally-relevant public data and temporally-relevant medical data such as pollen counts for the area of residence of the patient, chronic issues for workers performing the type of work that the patient performs, chronic issues faced by individuals living in the geographical area of residence or location of the patient, local and regional pandemic updates during a time of pandemic, etc. The temporally-relevant public data and the temporally-relevant medical data may be referred to as temporal data. As part of step 218, the deep learning model holistically combines and integrates the multiple sets of patient data and medical services provider data that were received to help with production of both the first document and the second document. The combination and integration of the multiple sets of data occurs via the logic programmed into the two-way document generation program 110a, 110b, 110c.

In at least some embodiments, the one or more documents produced that are tailored to be read or listened to by the patient include questions which request information about symptoms being experienced by the patient. In embodiments where patient symptom information was already provided along with the request of step 212, the document for the patient may include follow-up questions related to the symptoms.

In at least some embodiments the one or more documents produced that are tailored to be read or listened to by the patient include a questionnaire that includes at least one question for the patient. The document or questionnaire may include one or more questions related to patient symptoms, patient medical history, patient background such as education, occupation, family situation, and residence, diet of the patient, exercise routines of the patient, risk profile of the patient, insurance coverage of the patient, payment preferences of the patient, allergies of the patient, medications currently taken by the patient, and health treatment preferences of the patient. For example, the document or questionnaire may ask the patient whether they prefer surgical treatment options or non-surgical treatment options.

The two-way document generation program 110c may generate the document in digital form that can be sent to another computer via the communication network 116 or that may be sent to a printer connected to the server 112. The document to be generated for the patient, e.g., the first document, may include a number of questions on one page of the document or may include one question only on each page of a document. The document may be a single-page document or be a multi-page document. In some embodiments, for example, when a patient is blind or has sight-impairment, the document for the patient may include an audio message to accompany or replace a digital document that can be seen.

The first document produced for the patient may also include information to assist the patient such as a physical address of the medical services provider, information about a time and/or date for an appointment of the patient to see the medical services provider, and/or current travel conditions, e.g., weather or road conditions, for the areas at and between the location of the patient (potential patient) and the office of the medical services provider. The document produced for the patient may also include all or some of the temporally-relevant public data and temporally-relevant medical data that was retrieved by web crawling or web scraping during step 218 according to the model training that was provided in step 210. For example, the first document may include information about current pollen counts in the area of the patient, about air quality levels in the area of the patient, and pandemic updates in times of pandemics.

In some embodiments, the first document is presented to the patient in a dynamic manner. The dynamic presentation incudes the first document being presented as multiple pages or multiple sections, and a single page or a portion less than all of the multiple pages is transmitted and presented to the patient in a first instance. This dynamic presentation also may include a connection being maintained between a computer of the patient, e.g., the first computer 102a, and a computer of the two-way document generation program 110c, e.g., the server 112. Such a lingering connection may, for example, be maintained via the connection network 116. As part of this dynamic presentation, the two-way document generation program 110c can promptly receive answers from the patient that the patient provides in response to one or more questions that were presented on the first page or the first portion of the first document. Then, based on this response or this answer, the two-way document generation program 110c generates the questions on the second page or on the second portion of the first document that are thereafter presented to the patient after transmittal through the connection network 116.

Based on the responses or answers of the patient in this dynamic production and presentation of the patient document, some typical questions for a patient questionnaire may be skipped, as the responses or answers may reveal to the two-way document generation program 110c that certain other questions are irrelevant to this particular patient. Based on the responses or answers of the patient, some atypical questions for a patient questionnaire may be added, as the responses or answers to the first portion or first page may reveal to the two-way document generation program 110c that certain other questions are relevant to this particular patient.

As part of the dynamic production and presentation of the patient document or the patient questionnaire, the two-way document generation program 110c may recognize in responses from the patient that the patient is not fully understanding the questions. In those instances, the two-way document generation program 110c can generate subsequent portions or pages of the patient document in a manner that simplifies language, repeats questions if necessary, and even repeats questions using alternative language if necessary.

In some instances when the two-way document generation program 110c receives quick responses from the patient to questions from the patient questionnaire, the two-way document generation program 110c may use those responses to help focus information or questions that are added to a portion of the second document generated for and presented to the medical services provider. For example if a patient provides clarifying responses regarding symptoms the patient is experiencing, the two-way document generation program 110c may rule out and replace some possible medications or treatment options that otherwise would be presented to the medical services provider on the second document—on the document or documents to be presented to the medical services provider.

In at least some embodiments the at least one document, e.g., the second document, that is tailored to be read or listened to by the medical services provider may include the patient data or some of the patient data including patient symptoms, patient medical history, patient background such as education, occupation, family situation, and residence, diet of the patient, exercise routines of the patient, insurance coverage of the patient, payment preferences of the patient, allergies of the patient, medications currently taken by the patient, and health treatment preferences of the patient. For example, the document to be provided to the medical services provider may also include all or some of the patient data that was submitted along with the request from step 212. When the patient has previously used the two-way document generation program 110a, 110b, 110c, the two-way document generation program 110c may have more patient data about a particular patient as compared to those instances when a patient for the first time interacts with the two-way document generation program 110c. For prior patients, the two-way document generation program 110c may have some patient data saved in the database 114. The document to be provided to the medical services provider may also include some patient data that was with the patient or with the two-way document generation program 110a when the request was submitted in step 212.

The document produced for the medical services provider may also include all or some of the temporally-relevant public data and temporally-relevant medical data that was retrieved by web crawling or web scraping during step 218 according to the model training that was provided in step 210. The machine learning model may match the temporally-relevant public data and temporally-relevant medical data with all or some of the patient data to parse out public and temporal data which have heightened relevancy to a patient. For example, if a patient has symptoms that may be interpreted as being possibly caused by allergies and if the temporally-relevant data indicated a high pollen count in the area of the patient over the previous time period, e.g., over the previous days, then the document for the medical services provider may list the pollen-count for the area and may list this as being a possible cause of symptoms of the patient. If the patient data includes symptoms of the patient and if the machine learning model matches the symptoms with one or more possible diseases or negative health conditions, the document produced for the medical services provider may list or include the possible diseases or negative health conditions as well as possible treatments for the patient to mitigate or remedy the diseases.

The document to be provided to the medical services provider may include a question asking whether the medical services provider prefers surgical treatment options or non-surgical treatment options as a first choice for patients. Therefore, in this embodiment the document provided for the medical services provider may also be considered a questionnaire because it contains at least one question. This embodiment may include a dynamic presentation of the document to the medical services provider, because the answer of the medical services provider to this question or another question may cause the two-way document generating program 110c to present different information in a subsequent portion of the second document or in a subsequent page of the second document.

For creating portions of the second documents, namely the documents produced for and presented to the medical services provider, the two-way document generating program 110c can also use any preference provided by the patient in the patient data or provided by the patient in response to the patient document. This patient preference may help in the second document for organizing possible treatment recommendations that are provided to the medical services provider on a subsequent page of the document or on an additional document that is sent to the medical services provider by the two-way document generating program 110c.

The two-way document generation program 110c may, in digital form, generate the document for the medical services provider and may send that digital document to another computer, e.g., to the second computer 102b, via the communication network 116 or to a printer connected to the server 112. The document to be generated for the medical services provider, e.g., the second document, may include a number of questions or pieces of information on one page of the document or may include one question or item of information only on each page of a document. A question or questions that is/are on the medical services provider document may be intended for the medical services provider, e.g., the doctor, as an appropriate question to ask the patient during a medical services visit that the patient makes to the medical services provider, e.g., to the doctor.

The document for the medical services provider may be a single-page document or be a multi-page document. In some embodiments, for example, when a medical services provider is blind or has sight-impairment, the document for the medical services provider may include an audio message to accompany or replace a digital document that can be seen.

The two-way document generation program 110c may also produce the first and second documents according to a language or foreign language speaking needs of patients or medical services providers, according to reading literacy levels of a patient, and according to computer literacy levels of a patient or a medical services provider.

In step 220 of process 200 shown in FIG. 2, the first document is presented to the patient and the second document is presented to the medical services provider. This presentation of step 220 may occur via a digital representation on a display screen of the first computer 102a and/or of the second computer 102b. The first and the second documents may be sent from the server 112 to the first computer 102a and to the second computer 102b via the communication network 116. The document may be sent via an email or via an SMS message and may be sent with a notification signal that will cause the first computer 102a and/or the second computer 102b to notify a user that the document has been received by the first computer 102a or the second computer 102b. For example, the document files may trigger the first and second computers 102a, 102b to beep, buzz, flash lights, and/or ring when the document files are received. For those embodiments in which the documents include some audio component, the presentation of step 220 may include an audio presentation of the audio component via a speaker of the first computer 102a or of the second computer 102b.

In instances where the patient holds or possesses the first computer 102a and the medical services provider holds or possesses the second computer 102b, step 220 may be performed by displaying the first document on a display screen of the first computer 102a and by displaying the second document on a display screen of the second computer 102b.

When the document for the patient is a questionnaire, the patient may answer the questions of the questionnaire and may cause the two-way document generation program 110a to transmit the answers back over the communication network 116 to be received by the two-way document generation program 110c in the server 112 and then subsequently, via the server 112 and the communication network 116, to the two-way document generation program 110b of the second computer 102b of the medical services provider.

In step 222 of process 200 shown in FIG. 2, feedback is received from the patient and from the medical services provider. This feedback may be performed by the patient and/or the medical services provider providing responses to any questions on the documents or questionnaires and returning same to the two-way document generation program 110c at the server 112. The feedback may also be affected by the two-way document generation program 110a, 110b, 110c generating a survey to ask the patient or the medical services provider whether the documents that were produced and represented were helpful or easily understood by the reader.

In step 224 of process 200 shown in FIG. 2, the feedback is fed to the machine learning model. As part of step 224, the feedback received in step 222 is loaded into or fed to the machine learning model. Feedback provided from the patient at a first computer 102a may be transmitted via the communication network 116 to the two-way document generation program 110c at the server 112 where the program of the machine learning model may be hosted. Feedback provided from the medical services provider at a second computer 102b may be transmitted via the communication network 116 to the two-way document generation program 110c at the server 112 where the program of the machine learning model may be hosted.

Because the step 224 of the process 200 then leads to a repeat of the step of 210 of training the machine learning model, the feeding of the feedback to the machine learning model may help the machine learning model to make updates to its internal algorithms and/or layers to make corrections to or improvements for the program based on the feedback.

The cycle can be repeated so that the process can help improve communication for future patient-doctor interactions of the same patient, so that machine learning model advances for one patient may also be used to help medical communication for other patients and other medical services providers, and also so that the machine learning model is continually improved and trained with new information.

With the above-described solutions, embodiments of the present disclosure improve the technical field of medical artificial intelligence by improving patient-doctor communication and improving the benefits and effectiveness of patient-doctor one-on-one time. Embodiments of the present disclosure help doctors and medical services providers receive more information from patients and thereby help medical services providers more quickly bring effective medical advice, effective medical treatments, and relief to patients. Embodiments of the present disclosure also help improve medical literacy of patients.

Figure 3:
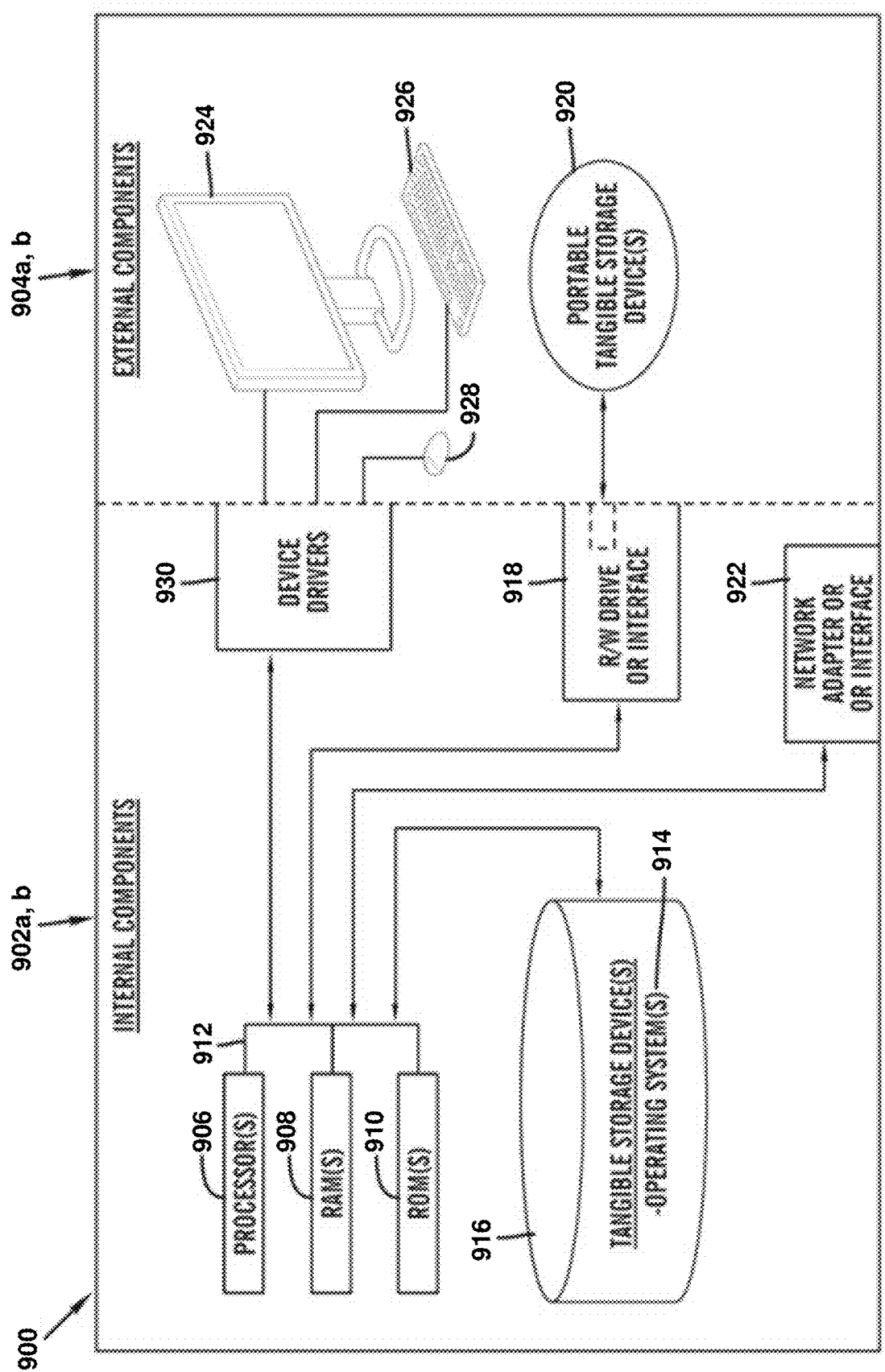
FIG. 3 is a block diagram of internal and external components of computers and servers depicted in FIG. 1 according to at least one embodiment.

FIG. 3 is a block diagram 900 of internal and external components of computers depicted in FIG. 1 in accordance with an illustrative embodiment of the present invention. It should be appreciated that FIG. 3 provides only an illustration of one implementation and does not imply any limitations with regard to the environments in which different embodiments may be implemented. Many modifications to the depicted environments may be made based on design and implementation requirements.

Data processing system 902, 904 is representative of any electronic device capable of executing machine-readable program instructions. Data processing system 902, 904 may be representative of a smart phone, a computer system, PDA, or other electronic devices. Examples of computing systems, environments, and/or configurations that may be represented by data processing system 902, 904 include, but are not limited to, personal computer systems, server computer systems, thin clients, thick clients, hand-held or laptop devices, multiprocessor systems, microprocessor-based systems, network PCs, minicomputer systems, and distributed cloud computing environments that include any of the above systems or devices.

First computer 102a, second computer 102b, and server 112 may include respective sets of internal components 902a, 902b and external components 904a, 904b illustrated in FIG. 3. Each of the sets of internal components 902a, 902b includes one or more processors 906, one or more computer-readable RAMs 908 and one or more computer-readable ROMs 910 on one or more buses 912, and one or more operating systems 914 and one or more computer-readable tangible storage devices 916. The one or more operating systems 914, the software program 108, the two-way document generation program 110a in the first computer 102a, the two-way document generation program 110b in the second computer 102b, and the two-way document generation program 110c in network server 112, may be stored on one or more computer-readable tangible storage devices 916 for execution by one or more processors 906 via one or more RAMs 908 (which typically include cache memory). In the embodiment illustrated in FIG. 3, each of the computer-readable tangible storage devices 916 is a magnetic disk storage device of an internal hard drive. Alternatively, each of the computer-readable tangible storage devices 916 may be a semiconductor storage device such as ROM 910, EPROM, flash memory or any other computer-readable tangible storage device that can store a computer program and digital information.

Each set of internal components 902a, 902b also includes a R/W drive or interface 918 to read from and write to one or more portable computer-readable tangible storage devices 920 such as a CD-ROM, DVD, memory stick, magnetic tape, magnetic disk, optical disk or semiconductor storage device. A software program, such as the software program 108 and the two-way document generation program 110a, 110b, 110c can be stored on one or more of the respective portable computer-readable tangible storage devices 920, read via the respective R/W drive or interface 918 and loaded into the respective hard drive 916.

Each set of internal components 902a, 902b may also include network adapters (or switch port cards) or interfaces 922 such as a TCP/IP adapter cards, wireless wi-fi interface cards, or 3G or 4G wireless interface cards or other wired or wireless communication links. The software program 108 and the two-way document generation program 110a in first computer 102a, the two-way document generation program 110b in second computer 102b, and the two-way document generation program 110c in server 112 can be downloaded from an external computer (e.g., server) via a network (for example, the Internet, a local area network or other, wide area network) and respective network adapters or interfaces 922. From the network adapters (or switch port adaptors) or interfaces 922, the software program 108 and the two-way document generation program 110a in first computer 102a, the two-way document generation program 110b in second computer 102b, and the two-way document generation program 110c in server 112 are loaded into the respective hard drive 916. The network may include copper wires, optical fibers, wireless transmission, routers, firewalls, switches, gateway computers and/or edge servers.

Each of the sets of external components 904a, 904b can include a computer display monitor 924, a keyboard 926, and a computer mouse 928. External components 904a, 904b can also include touch screens, virtual keyboards, touch pads, pointing devices, speakers, and other human interface devices. Each of the sets of internal components 902a, 902b also includes device drivers 930 to interface to computer display monitor 924, keyboard 926 and computer mouse 928. The device drivers 930, R/W drive or interface 918 and network adapter or interface 922 comprise hardware and software (stored in storage device 916 and/or ROM 910).

The present invention may be a system, a method, and/or a computer program product at any possible technical detail level of integration. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punchcards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be accomplished as one step, executed concurrently, substantially concurrently, in a partially or wholly temporally overlapping manner, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

It is understood that although this disclosure includes a detailed description on cloud computing, implementation of the teachings recited herein are not limited to a cloud computing environment. Rather, embodiments of the present invention are capable of being implemented in conjunction with any other type of computing environment now known or later developed.

Cloud computing is a model of service delivery for enabling convenient, on-demand network access to a shared pool of configurable computing resources (e.g., networks, network bandwidth, servers, processing, memory, storage, applications, virtual machines, and services) that can be rapidly provisioned and released with minimal management effort or interaction with a provider of the service. This cloud model may include at least five characteristics, at least three service models, and at least four deployment models.

Characteristics are as follows:

On-demand self-service: a cloud consumer can unilaterally provision computing capabilities, such as server time and network storage, as needed automatically without requiring human interaction with the service's provider.

Broad network access: capabilities are available over a network and accessed through standard mechanisms that promote use by heterogeneous thin or thick client platforms (e.g., mobile phones, laptops, and PDAs).

Resource pooling: the provider's computing resources are pooled to serve multiple consumers using a multi-tenant model, with different physical and virtual resources dynamically assigned and reassigned according to demand. There is a sense of location independence in that the consumer generally has no control or knowledge over the exact location of the provided resources but may be able to specify location at a higher level of abstraction (e.g., country, state, or datacenter).

Rapid elasticity: capabilities can be rapidly and elastically provisioned, in some cases automatically, to quickly scale out and rapidly released to quickly scale in. To the consumer, the capabilities available for provisioning often appear to be unlimited and can be purchased in any quantity at any time.

Measured service: cloud systems automatically control and optimize resource use by leveraging a metering capability at some level of abstraction appropriate to the type of service (e.g., storage, processing, bandwidth, and active user accounts). Resource usage can be monitored, controlled, and reported providing transparency for both the provider and consumer of the utilized service.

Service Models are as follows:

Software as a Service (SaaS): the capability provided to the consumer is to use the provider's applications running on a cloud infrastructure. The applications are accessible from various client devices through a thin client interface such as a web browser (e.g., web-based e-mail). The consumer does not manage or control the underlying cloud infrastructure including network, servers, operating systems, storage, or even individual application capabilities, with the possible exception of limited user-specific application configuration settings.

Platform as a Service (PaaS): the capability provided to the consumer is to deploy onto the cloud infrastructure consumer-created or acquired applications created using programming languages and tools supported by the provider. The consumer does not manage or control the underlying cloud infrastructure including networks, servers, operating systems, or storage, but has control over the deployed applications and possibly application hosting environment configurations.

Infrastructure as a Service (IaaS): the capability provided to the consumer is to provision processing, storage, networks, and other fundamental computing resources where the consumer is able to deploy and run arbitrary software, which can include operating systems and applications. The consumer does not manage or control the underlying cloud infrastructure but has control over operating systems, storage, deployed applications, and possibly limited control of select networking components (e.g., host firewalls).

Deployment Models are as follows:

Private cloud: the cloud infrastructure is operated solely for an organization. It may be managed by the organization or a third party and may exist on-premises or off-premises.

Community cloud: the cloud infrastructure is shared by several organizations and supports a specific community that has shared concerns (e.g., mission, security requirements, policy, and compliance considerations). It may be managed by the organizations or a third party and may exist on-premises or off-premises.

Public cloud: the cloud infrastructure is made available to the general public or a large industry group and is owned by an organization selling cloud services.

Hybrid cloud: the cloud infrastructure is a composition of two or more clouds (private, community, or public) that remain unique entities but are bound together by standardized or proprietary technology that enables data and application portability (e.g., cloud bursting for load-balancing between clouds).

A cloud computing environment is service oriented with a focus on statelessness, low coupling, modularity, and semantic interoperability. At the heart of cloud computing is an infrastructure comprising a network of interconnected nodes.

Figure 4:
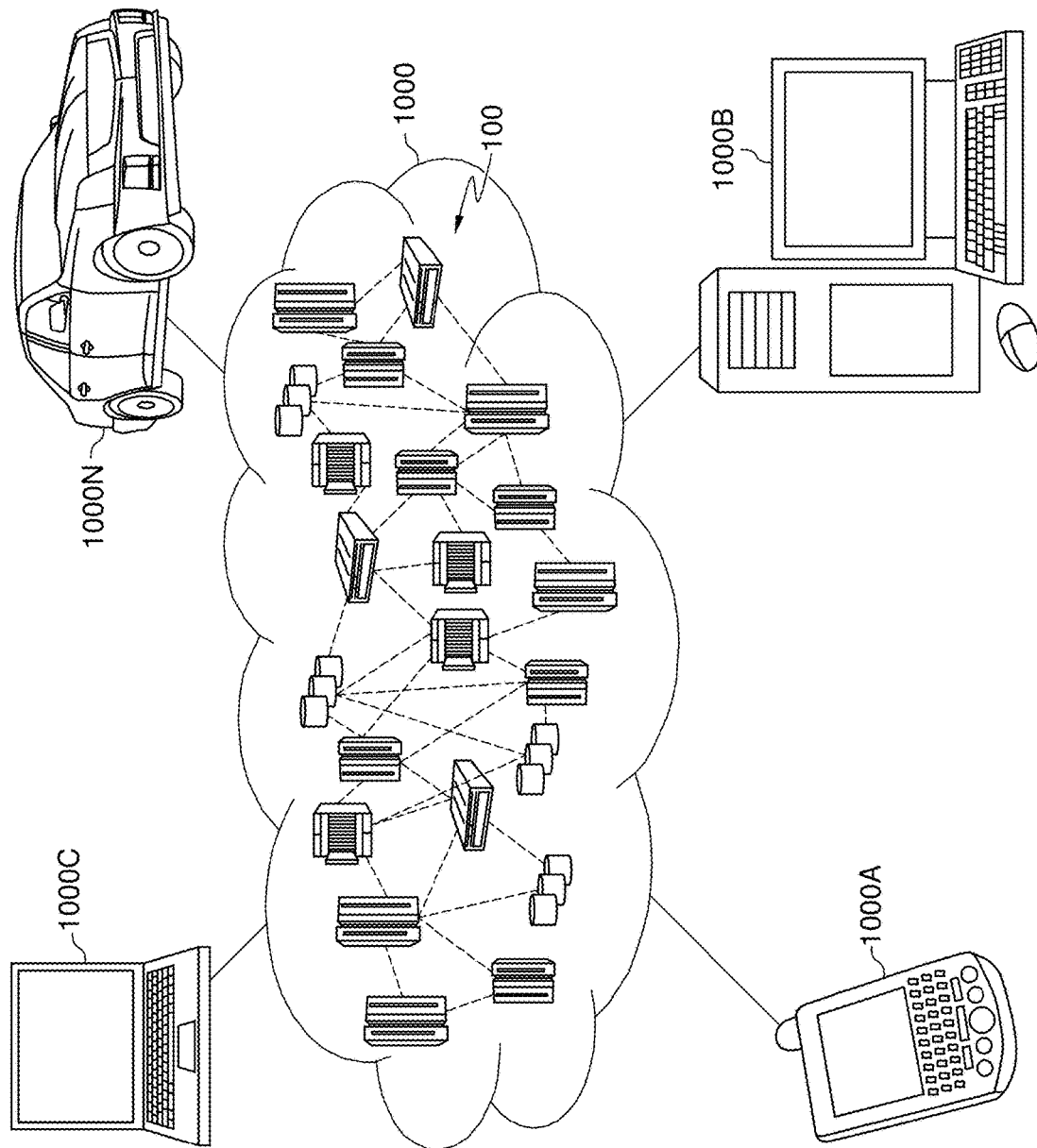
FIG. 4 is a block diagram of an illustrative cloud computing environment including the computer system depicted in FIG. 1, in accordance with an embodiment of the present disclosure.

Referring now to FIG. 4, illustrative cloud computing environment 1000 is depicted. As shown, cloud computing environment 1000 comprises one or more cloud computing nodes 100 with which local computing devices used by cloud consumers, such as, for example, personal digital assistant (PDA) or cellular telephone 1000A, desktop computer 1000B, laptop computer 1000C, and/or automobile computer system 1000N may communicate. Nodes 100 may communicate with one another. They may be grouped (not shown) physically or virtually, in one or more networks, such as Private, Community, Public, or Hybrid clouds as described hereinabove, or a combination thereof. This allows cloud computing environment 1000 to offer infrastructure, platforms and/or software as services for which a cloud consumer does not need to maintain resources on a local computing device. It is understood that the types of computing devices 1000A-N shown in FIG. 4 are intended to be illustrative only and that computing nodes 100 and cloud computing environment 1000 can communicate with any type of computerized device over any type of network and/or network addressable connection (e.g., using a web browser).

Figure 5:
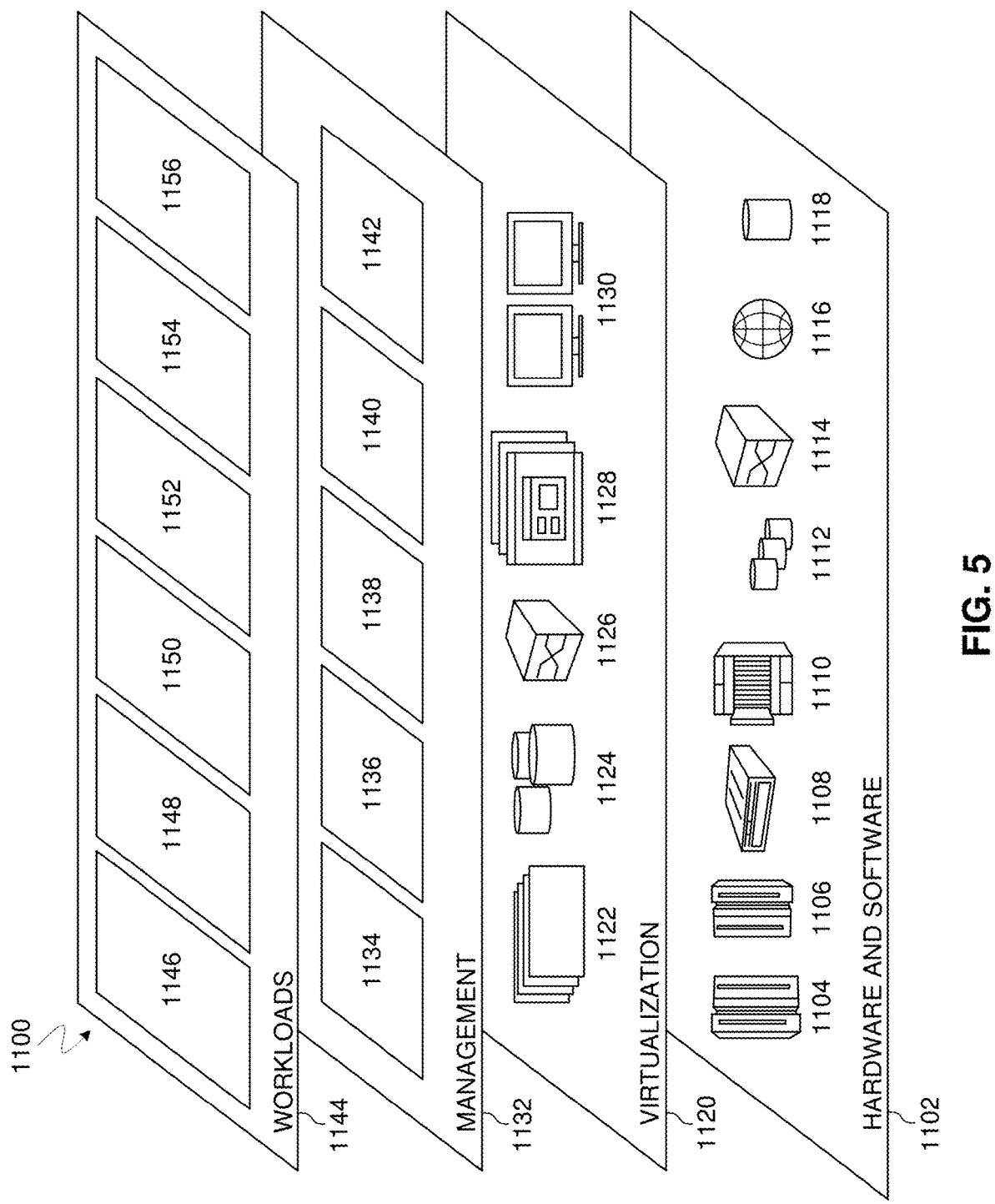
FIG. 5 is a block diagram of functional layers of the illustrative cloud computing environment of FIG. 4, in accordance with an embodiment of the present disclosure.

Referring now to FIG. 5, a set of functional abstraction layers 1100 provided by cloud computing environment 1000 is shown. It should be understood in advance that the components, layers, and functions shown in FIG. 5 are intended to be illustrative only and embodiments of the invention are not limited thereto. As depicted, the following layers and corresponding functions are provided:

Hardware and software layer 1102 includes hardware and software components. Examples of hardware components include: mainframes 1104; RISC (Reduced Instruction Set Computer) architecture based servers 1106; servers 1108; blade servers 1110; storage devices 1112; and networks and networking components 1114. In some embodiments, software components include network application server software 1116 and database software 1118.

Virtualization layer 1120 provides an abstraction layer from which the following examples of virtual entities may be provided: virtual servers 1122; virtual storage 1124; virtual networks 1126, including virtual private networks; virtual applications and operating systems 1128; and virtual clients 1130.

In one example, management layer 1132 may provide the functions described below. Resource provisioning 1134 provides dynamic procurement of computing resources and other resources that are utilized to perform tasks within the cloud computing environment. Metering and Pricing 1136 provide cost tracking as resources are utilized within the cloud computing environment, and billing or invoicing for consumption of these resources. In one example, these resources may comprise application software licenses. Security provides identity verification for cloud consumers and tasks, as well as protection for data and other resources. User portal 1138 provides access to the cloud computing environment for consumers and system administrators. Service level management 1140 provides cloud computing resource allocation and management such that required service levels are met. Service Level Agreement (SLA) planning and fulfillment 1142 provide pre-arrangement for, and procurement of, cloud computing resources for which a future requirement is anticipated in accordance with an SLA.

Workloads layer 1144 provides examples of functionality for which the cloud computing environment may be utilized. Examples of workloads and functions which may be provided from this layer include: mapping and navigation 1146; software development and lifecycle management 1148; virtual classroom education delivery 1150; data analytics processing 1152; transaction processing 1154; and two-way document generation 1156. A two-way document generation program 110*a*, 110*b*, 110*c* provides a way to improve medical communication between a patient and a medical services provider.

The terminology used herein is for the purpose of describing particular embodiments only and is not intended to be limiting of the invention. As used herein, the singular forms "a," "an," and "the" are intended to include the plural forms as well, unless the context clearly indicates otherwise. It will be further understood that the terms "comprises," "comprising," "includes," "including," "has," "have," "having," "with," and the like, when used in this specification, specify the presence of stated features, integers, steps, operations, elements, and/or components, but does not preclude the presence or addition of one or more other features, integers, steps, operations, elements, components, and/or groups thereof.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope of the described embodiments. The terminology used herein was chosen to best explain the principles of the embodiments, the practical application or technical improvement over technologies found in the marketplace, or to enable others of ordinary skill in the art to understand the embodiments disclosed herein.

What is claimed is:

1. A computer-implemented method comprising:
    training, via the one or more processors, a machine learning model in a supervised manner by providing to the machine learning model gathered medical information and sample sets of generated patient documents and medical services provider data documents based on certain input data;
    receiving, via one or more processors, patient data from a patient and medical services provider data from a medical services provider;
    crawling, via the one or more processors, the Internet to gather first temporal data that pertains to chronic issues for workers of different types of work;
    matching, via the one or more processors, the gathered first temporal data to a type of work that the patient performs as indicated from the patient data;
    running, via the one or more processors, the patient data and the medical services provider data through the trained machine learning model so that the trained machine learning model produces a first document comprising the matched first temporal data and a second document;
    transmitting the first document to a first computer for presentation to the patient; and
    transmitting the second document to a second computer for presentation to the medical services provider.

2. The method according to claim 1, wherein the first document is a questionnaire.

3. The method according to claim 1, wherein the matched first temporal data is included as part of the second document.

4. The method according to claim 1, further comprising receiving, via the one or more processors, a document-generation request, wherein at least some of the patient data is received along with the document-generation request.

5. The method according to claim 1, further comprising:
    receiving from the patient, via the one or more processors, feedback to the first document;
    wherein the second document is produced using the feedback to the first document.

6. The method according to claim 1, wherein the second document includes at least one question for the medical services provider to ask the patient during a medical exam.

7. A computer system for two-way document generation for medical communication, the computer system comprising:
    one or more processors, one or more computer-readable memories, one or more computer-readable tangible storage media, and program instructions stored on at least one of the one or more computer-readable tangible storage media for execution by at least one of the one or more processors via at least one of the one or more computer-readable memories, wherein the computer system is capable of performing a method comprising:
        training a machine learning model in a supervised manner by providing to the machine learning model gathered medical information and sample sets of generated patient documents and medical services provider data documents based on certain input data;
        receiving patient data from a patient and medical services provider data from a medical services provider;
        crawling the Internet to gather first temporal data that pertains to chronic issues for workers of different types of work;
        matching the gathered first temporal data to a type of work that the patient performs as indicated from the patient data;
        running the patient data and the medical services provider data through the trained machine learning model so that the trained machine learning model produces a first document comprising the matched first temporal data and a second document;
        transmitting the first document to a first computer for presentation to the patient; and
        transmitting the second document to a second computer for presentation to the medical services provider.

8. The computer system according to claim 7, wherein the method further comprises receiving, from the patient, feedback to the first document; and
    wherein the second document is produced using the feedback to the first document.

9. The computer system according to claim 7, wherein the second document includes at least one question for the medical services provider to ask the patient during a medical exam.

10. A computer program product for two-way document generation for medical communication, the computer program product comprising a computer-readable storage medium having program instructions embodied therewith, the program instructions being executable processor to cause the processor to perform a method comprising:
    training a machine learning model in a supervised manner by providing to the machine learning model gathered medical information and sample sets of generated patient documents and medical services provider data documents based on certain input data;
    receiving patient data from a patient and medical services provider data from a medical services provider;
    crawling the Internet to gather first temporal data that pertains to chronic issues for workers of different types of work;
    matching the gathered first temporal data to a type of work that the patient performs as indicated from the patient data;
    running the patient data and the medical services provider data through the trained machine learning model so that the trained machine learning model produces a first document comprising the matched first temporal data and a second document;
    transmitting the first document to a first computer for presentation to the patient; and transmitting the second document to a second computer for presentation to the medical services provider.

11. The computer program product according to claim 10, wherein the matched first temporal data is included as part of the second document.

12. The computer program product according to claim 10, wherein the method further comprises receiving a document-generation request; and wherein at least some of the patient data is received along with the document-generation request.

13. The method according to claim 1, wherein the first document comprises current travel conditions between a current location of the patient and a current location of the medical services provider.

14. The method according to claim 1, wherein at least one of the first document and the second document comprises a question requesting a preference for a surgical option or a non-surgical medical treatment.

15. The method according to claim 1, further comprising:
crawling, via the one or more processors, the Internet to gather second temporal data that pertains to medical conditions associated with geographic areas; and matching, via the one or more processors, the gathered second temporal data to a geographic area of the patient as indicated by the patient data;

wherein the first document further comprises the matched second temporal data.

16. The method according to claim 1, wherein the training of the machine learning model in the supervised manner further comprises expert verification of an appropriate level of detail for the second document based on a role of the medical services provider.

17. The method according to claim 1, wherein the first document comprises a digital document and an audio message.

18. The method according to claim 15, wherein the matched second temporal data is selected from the group consisting of: environmental conditions for the geographical area of the patient, chronic issues faced by individuals in the geographical area of the patient, and pandemic updates based on the geographical area of the patient.

19. The method according to claim 18, wherein the environmental conditions are selected from a group consisting of air quality, a pollen count, and weather.

\* \* \* \* \*